(12) United States Patent
Jira et al.

(10) Patent No.: US 7,914,799 B2
(45) Date of Patent: Mar. 29, 2011

(54) ANTI-FUNGAL COMPOSITION

(75) Inventors: Vic Jira, El Monte, CA (US); Vichai Jirathitikal, Chachoengsao (TH)

(73) Assignee: Immunitor USA, Inc., College Park, MD (US)

( * ) Notice: Subject to any disclaimer, the term of this patent is extended or adjusted under 35 U.S.C. 154(b) by 433 days.

(21) Appl. No.: 10/228,280

(22) Filed: Aug. 27, 2002

(65) Prior Publication Data

US 2003/0039667 A1 Feb. 27, 2003

Related U.S. Application Data

(60) Provisional application No. 60/314,666, filed on Aug. 27, 2001.

(51) Int. Cl.
*A61K 39/00* (2006.01)
*A61K 45/00* (2006.01)
*A01N 63/00* (2006.01)

(52) U.S. Cl. .................. 424/274.1; 424/184.1; 424/93.5; 424/278.1

(58) Field of Classification Search .............. 424/274.1, 424/184.1, 93.5, 93.51; 530/823, 824
See application file for complete search history.

(56) References Cited

U.S. PATENT DOCUMENTS

| | | | |
|---|---|---|---|
| 4,229,434 A | 10/1980 | Sarkisov et al. | 424/88 |
| 4,368,191 A | 1/1983 | Sarkisov et al. | 424/88 |
| 5,003,750 A * | 4/1991 | Delgado | 52/741.11 |
| 5,277,904 A | 1/1994 | Pier | 424/88 |
| 5,284,652 A | 2/1994 | Pier | |
| 5,320,849 A * | 6/1994 | Hagiwara et al. | 424/442 |
| 5,453,273 A | 9/1995 | Werner et al. | 424/274.1 |
| 5,641,761 A * | 6/1997 | Takahashi et al. | 514/54 |
| 5,817,643 A * | 10/1998 | Jamas et al. | 514/54 |
| 5,858,378 A * | 1/1999 | Bostwick | 424/274.1 |
| 5,948,413 A | 9/1999 | Mendoza | 424/274.1 |
| 6,007,809 A * | 12/1999 | Chaykin | 424/93.51 |
| 6,020,324 A * | 2/2000 | Jamas et al. | 514/54 |
| 6,132,733 A | 10/2000 | Werner et al. | 424/274.1 |
| 6,333,164 B1 * | 12/2001 | Takesako et al. | 435/7.3 |
| 6,551,600 B2 * | 4/2003 | Hawkins et al. | 424/278.1 |
| 6,939,864 B1 * | 9/2005 | Johnson et al. | 514/54 |
| 2002/0119928 A1 * | 8/2002 | McAnalley | 514/12 |

FOREIGN PATENT DOCUMENTS

| | | | |
|---|---|---|---|
| CS | 277 558 | * | 2/1993 |
| CS | 277558 | * | 2/1993 |
| EP | 0555618 A2 | * | 8/1993 |
| JP | 60126223 A | * | 7/1985 |
| JP | 402218615 A | * | 8/1990 |
| WO | WO 9735596 A1 | * | 10/1997 |
| WO | WO 99/38529 | * | 8/1999 |

OTHER PUBLICATIONS

Markova et al. Int. J. Immunopharmac, 19: 205-214, 1997.*
Manual of Clinical Microbiology, III Edition (Ed) Lenette et al. ASM, Washington D.C., 1980, pp. 562,563 & 577.*
Ruedl et al. Clin. Diagn. Lab. Immunol. 1: 150-154, 1994.*
Rutishauser et al. Adv. Ther. 15: 330-341, 1998.*
Cassone et al. Infect. Immun. 63: 2619-2624, 1995.*
Elahi et al. Vaccine 19: 2516-2521, 2001.*
Nicoletti et al. Arzneimittelforschung 42: 1246-1250, 1992.*
Browder et al. Int. J. Immunopharmacol. 6: 19-26, 1984.*
Jensen et al. J. Infect. Dis. 174: 133-140, 1996.*
Williams et al. J. Reticuloendothel. Soc. 23: 479-490, 1978.*
Suzuki et al. Int. J. Immunopharmacol. 11: 761-769, 1989.*
IMeister et al. J. Infect. Dis. 135: 235-242, 1977.*
Salvaggio et al. J. Immunol. 100: 1340-1352, 1968.*
Kennedy et al. In: Bioactive Carbohydrates: In Chemistry, Biochemistry and Biology. John Wiley & Sons, New York, p. 308, 1984.*
Sakurai et al. Int. J. Pharmacol. 14: 821-830, 1992.*
Numata et al. Org. Lett. 25: 4447-4450, 2004, abstract.*
Koike K. Jpn. J. Antibiot. 29: 1098-1105, 1976, abstract.*
Marinova et al. Inter. J. Immunopharnacol. 22: 843-854, 2000.*
Cohen et al. Am. J. Health-System Pharmacy, posted Sep. 14, 2007.*
Hurtel et al. Infect. Immun. 31: 95-101, 1981.*
Burford-Mason et al. J. Infect. 14: 147-157, 1987.*
Levy et al. Vaccine 7: 337-340, 1989.*
Otero et al. J. Food Process. Preservat. 22: 419-432, 1998.*
Koukalova et al. English translation of CS 277 558, pp. 1-10, 1993.*
Koukalova et al. English translation of CS 277 558, pp. 1-9, 1993.*
Hida et al. Biol. Pharm. Bull. 30: 1589-1592, 2007, abstract.*
Kondori et al. APMIS 116: 867-876, 2008, abstract.*
Ishibashi et al. FEMS Immunology and Medical Microbiology 44: 99-109, 2005, abstract.*
Edgington et al. Mol. Cell. Biol. 19: 1369-1380, 1999, abstract.*
Bougnoux et al. J. Clin. Microbiol. 31: 1644-1645, 1993.*
Hazen et al. J. Clin. Microbiol. 37: 824-827, 1999, abstract.*
Tacket et al. Nat. Med. 4: 607-609, 1998, abstract.*
Tacket et al. Curr. Trop. Microbiol. Immunol. 332: 103-117, 2009, abstract.*
Arakawa et al. Nature Biotechnol. 16: 292-297, 1998, abstract.*
Stedman's Medical Dictionary, Williams & Wilkins, A Waverly Company, 26th Edition, pp. 29 and 853.
*Saccharomyces cerevisiae*, Retrieved from Internet: URL: http://en.wikipedia.org/wiki/Saccharomyces_cerevisiae, pp. 1-5.
Molds, Retrieved from URL Internet: http://en.wikipedia.org/wiki/Filamentous_fungi, pp. 1-5.
Ceccati-Antonini, et al., "Filamentous growth in *Saccharomyces cerevisiae*," Brazilian Journal of Microbiology, vol. 35, No. 3, (2004), pp. 1-16.
Pathogen, Retrieved from Internet URL: http://en.wikipedia.org/wiki/Pathogen.
Wordsmyth, Retrieved from Internet URL: http:www.wordsmyth.net/live/home.php?script=search&matchent=pathogen&matchtype.
Definition of Pathogen, Retrieved from MedicineNet.com, Internet URL: http://www.medterms.com/script/main/art.asp?articlekey=6383.

* cited by examiner

*Primary Examiner* — S. Devi
(74) *Attorney, Agent, or Firm* — Dykema Gossett PLLC

(57) ABSTRACT

A multivalent fungal vaccine comprising one or more heat-inactivated fungal antigens, wherein at least one fungal antigen is effective in producing an immune response in a host when said vaccine is administered orally at a dose that is sufficient for preventing or treating the fungal disease in said host. Also described are methods for making and using an orally available anti-fungal vaccine.

1 Claim, No Drawings

ANTI-FUNGAL COMPOSITION

This application claims priority of provisional application Ser. No. 60/314,666 filed Aug. 27, 2001.

FIELD OF THE INVENTION

The invention relates to an oral composition useful for treatment and prevention of fungal diseases. The invention also relates to process of making an orally available antifungal vaccine and methods of use.

BACKGROUND OF THE INVENTION

Pathogenic fungi occur worldwide and can cause diseases in humans, animals and plants. Fungal infections in humans range from superficial, i.e., skin surface to deeply invasive type or disseminated infection. Some of such infections especially those that are disseminated are fatal. Thus fungal diseases can be divided into the life-threatening systemic infections, such as histoplasmosis, systemic candidiasis, aspergillosis, blastomycosis, coccidioidomycosis, paracoccidioidomycosis, and cryptococcosis, and more common ones which are non-life-threatening, like dermatophyte (ringworm) infections, including tinea pedis (athlete's foot), tinea cruris (jock itch), candidiasis, and actinomycosis.

The life-threatening fungal infections are a growing problem not only for immunosuppressed or immunocompromised individuals but also in individuals with viral infections, such as cytomegalovirus (CMV), and influenza, for cancer patients receiving chemotherapy or radiotherapy, for transplant patients receiving antirejection agents, and for patients that have received toxic chemicals, metals and radiation exposure. Fungal opportunistic infections such as candidiasis, cryptococcosis, and histoplasmosis, occur frequently in patients with AIDS. Among the opportunistic infections, fungal infections caused by Pneumocystis, Candida, Cryptococcus, or Histoplasma are very common and prevalence can be as high as 85% among HIV-infected individuals. The incidence of systemic fungal infections increased 600% in teaching hospitals and 220% in non-teaching hospitals during the 1980's. The most common clinical isolate is *Candida albicans* (comprising about 19% of all isolates). Nearly 40% of all deaths from hospital-acquired infections were due to fungi.

The treatment of fungal infections has lagged behind bacterial chemotherapy. There are substantially fewer antifungal drugs than antibacterial drugs. The majority of known antifungal agents fall into one of three main groups. The major group includes polyene derivatives, including amphotericin B and the structurally related compounds nystatin and pimaricin, which are only administered intravenously. These are broad-spectrum antifungals that bind to ergosterol, a component of fungal cell membranes, and thereby disrupt the membranes, leading to cell death. Amphotericin B is usually effective for systemic mycoses, but its administration is limited by toxic effects that include fever and kidney damage, and other accompanying side effects such as anemia, low blood pressure, headache, nausea, vomiting and phlebitis. The unrelated antifungal agent flucytosine (5-fluorocytosine), an orally absorbed drug, is frequently used as an adjunct to amphotericin B treatment for some forms of candidiasis and cryptococcal meningitis. Its adverse effects include bone marrow depression with leukopenia and thrombocytopenia.

The second major group of antifungal agents includes azole derivatives which impair synthesis of ergosterol via lanosterol demethylase and lead to accumulation of metabolites that disrupt the function of fungal membrane-bound enzyme systems (e.g., cytochrome P450) and inhibit fungal growth. Significant inhibition of mammalian P450 results in important drug interactions. This group of agents includes ketoconazole, clotrimazole, miconazole, econazole, butoconazole, oxiconazole, sulconazole, terconazole, fluconazole and itraconazole. These agents may be administered to treat systemic mycoses. Ketoconazole, an orally administered imidazole, is used to treat nonmeningeal blastomycosis, histoplasmosis, coccidioidomycosis and paracoccidioidomycosis in non-immunocompromised patients, and is also useful for oral and esophageal candidiasis. Adverse effects include rare drug-induced hepatitis; ketoconazole is also contraindicated in pregnancy. Itraconazole appears to have fewer side effects than ketoconazole and is used for most of the same indications. Fluconazole also has fewer side effects than ketoconazole and is used for oral and esophageal candidiasis and cryptococcal meningitis. Miconazole is a parenteral imidazole with efficacy in coccidioidomycosis and several other mycoses, but has side effects including hyperlipidemia and hyponatremia.

The third major group of antifungal agents includes allylamnines-thiocarbamates, which are generally used to treat skin infections. This group includes tolnaftate and naftifine. Another antifungal agent is griseoflulvin, a fungistatic agent which is administered orally for fungal infections of skin, hair or nails that do not respond to topical treatment.

Limitations of current therapeutic options include: inadequate spectrum of activity, lack of efficacy due to growing resistance, poor safety profile, multiple drug interactions, inadequate pharmacokinetic profile, and excessive cost. Development of antifungal agents is a challenge because there are very few potential drug targets unique to fungi. Experts in fungal field agree that new drugs needs to be developed. Three novel azoles that offer improved potency and a wide spectrum of activity are in late-stage development: voriconazole, posaconazole, and ravuconazole. Another new class of agents, the candins—are a novel generation of cell-wall active semisynthetic 1,3 beta-glucan inhibitors—caspofungin, micafungin, and anidulafungin. There is also so-called Nyotran, a novel liposomal formulation of nystatin. In addition, a new class of protein synthesis inhibitors, the sordarins, are in preclinical development. Resistance to antifungals has become more apparent in recent years and may worsen with the increase in prophylatic therapy even with new drugs being developed. A small number of experts believe that in addition to new drug discovery strategy an alternative strategy for overcoming this and other problems is development of a vaccine.

A number of fungal vaccines have been proposed in the past: U.S. Pat. Nos. 4,229,434 and 4,368,191 issued to Sarkisov et al., disclose a live fungus vaccine for prophylaxis and treatment of trichopytosis caused by Trichophyton mentagrophytes. U.S. Pat. Nos. 5,277,904 and 5,284,652 issued to Pier disclose a broad spectrum dermatophyte vaccine for the prophylaxis of dermatophyte infection in animals, such as guinea pigs, cats, rabbits, horses and lambs. This vaccine comprises a suspension of killed *T. equinum, T. mentagrophytes* (var. granulare), *M. canis* and *M. gypseum* in an effective amount combined with an adjuvant. U.S. Pat. Nos. 5,453,273 and 6,132,733 issued to Werner et al., disclose a ringworm vaccine comprising an effective amount of a homogenized, formaldehyde-killed fungi, i.e., *Microsporum canis* culture in a carrier. U.S. Pat. No. 5,948,413 issued to Mendoza discloses a method and vaccine for treatment of pythiosis in humans and animals. Vaccine comprises a mixture of extracellular and intracellular proteins and enables cures of chronic pythiosis. However, the number of patents relating to a fungal vaccine is much smaller than those disclosing new antifungal drugs. Most of vaccine work was done by scientists who were outside of mainstream of fungal drug developers since fungal experts' establishment was not really concerned or convinced by the idea that vaccines would work.

Indeed only two commercial antifungal vaccines are currently available. The pioneering work in the former Soviet Union has resulted in ringworm vaccine for cattle which is sold as Ringvac bovis LTF-130 (Alpharma, Oslo, Norway). Another veterinarian vaccine similar to Soviet live vaccine is Czech live vaccine Bioveta (Bioveta, Ivanovice na Hane, Czech Republic).

While thus there are commercial fungal vaccines and experimental prototype vaccines which have potential therapeutic and prophylactic properties, without exception, they are all delivered by an injection. No oral fungal vaccines with proven clinical benefit exist at the present time. This is mainly due to the deep-rooted conviction that vaccine antigens will degrade in the stomach and thus the activity of the vaccine will be annihilated effectively rendering such a vaccine useless. This notion applies not only to oral fungal vaccine but all other vaccines in general.

Currently scientists are trying to obviate this problem by developing special encapsulation means to prevent a vaccine degradation. However, oral vaccine development is proving lengthy and complex and, at the present time, there is no completely satisfactory antifungal vaccine that is orally available.

The incidence of fungal infections caused by the opportunistic fungal infections has increased significantly in recent years. The use of antifungal drugs still causes major problems due to widespread drug resistance and the toxicity related effects of present chemotherapy. The availability of non-toxic and effective oral vaccine against pathogenic fungi would be advantageous. Present inventors have surprisingly discovered an effective broad-spectrum antifungal vaccine which is readily available orally.

SUMMARY OF THE INVENTION

The preferred embodiment of this invention comprises an oral antifungal vaccine prepared according to processes of the invention. Accordingly another embodiment provides a process of making oral antifungal vaccine that is effective against various fungal pathogens including but not limited to Dermatophytres like *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. album, var. discoides, var. ochraceum, *Trichophyton violaceum*, and/or *Trichophyton faviforme*, Other contemplated fungal pathogens comprise *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida parakawsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Paracoccidioides brasiliensis, Pneumocystis carinii, Pythium insidiosum, Pityrosporum ovale, Saccharomyces cerevisiae, Saccharomyces boulardii, Saccharomyces pombe, Scedosporium apiosperum, Sporothrix schenckii, Trichosporon beigelii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp.

The concept of present vaccine is directly applicable to fungi causing disease in plants. These parasites include fungi from genera like *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp. Due to immune cross-reaction between some of plant/food fungi with animal fungi these organisms are equally effective as immunogenic preparation for creating vaccine against human or veterinarian fungal infections.

The method for preparing the vaccine according to the present invention for prophylaxis and treatment of fungal infection involves growing the fungi of interest on a nutrient medium containing sources of carbon, nitrogen, and other biologically active ingredients to an optimal level, processing fungi such that obtained components thereof are not degradable upon oral absorption. In accordance with the present invention the immunogenic character of a specific fungus species, the suspension of fungus cells is lyzed, dried, and formulated into an oral pill preferably without any conventional immune adjuvant.

While preferred method of administering is oral other means of delivery, e.g., parenteral, are equally contemplated. Vaccine can be administered alone or together with other vaccines. Vaccine can be advantageously administered along with established and experimental antifungal drugs. Vaccine can be also administered with immune adjuvant. Non-limiting examples Quil A™, Freund's Incomplete Adjuvant, anhydrous lipids, cholera toxin produced by various strains of *Vibrio cholerae*, the heat-labile enterotoxin produced by some enterotoxigenic strains of *Escherichia coli*, and aluminum hydroxide among many others. Other strategies are not excluded to enhance the mucosal immunization, including the use of attenuated mutants of bacteria (e.g., *Salmonella* spp.) as carriers of heterologous antigens, encapsulation of antigens into microspheres, gelatin capsules, different formulations of liposomes, adsorption onto nanoparticles, use of lipophilic immune stimulating complexes, and addition of bacterial products with known adjuvant properties.

DETAILED DESCRIPTION OF THE INVENTION

Fungi are eukaryotic cells that may reproduce sexually or asexually and may be biphasic, with one form in nature and a different form in the infected host. Fungal diseases are referred to as mycoses. Some mycoses are endemic, i.e. infection is acquired in the geographic area that is the natural habitat of that fungus. These endemic mycoses are usually self-limited and minimally symptomatic. Some mycoses are chiefly opportunistic, occurring in immunocompromised patients such as organ transplant patients, cancer patients undergoing chemotherapy, burn patients, AIDS patients, or patients with diabetic ketoacidosis. Fungal infections are becoming a major health concern for a number of reasons, including the limited number of antifungal agents available, the increasing incidence of species resistant to older antifungal agents, and the growing population of immunocompromised patients at risk for opportunistic fungal infections. Neutropenic patients (due to, e.g., chemotherapy, immunosuppressive therapy, infection, including AIDS, or an otherwise dysfunctional immune system) are predisposed to the development of invasive fungal infections, most commonly including *Candida* species and *Aspergillus* species, and, on occasion, *Fusarium, Trichosporon* and *Dreschlera*. Cryptococcus infection is also common in patients on immunosuppressive agents. Histoplasmosis, caused by Histoplasma, is the most common endemic respiratory mycosis in the United States; over 40 million people have been infected. The disease is noncontagious and ordinarily self-limited, but chronic pulmonary infection and disseminated infection may occur. Pulmonary infection rarely requires treatment, but disseminated infection may be treated with amphotericin B. Coccidioidomycosis, caused by Coccidioides, is a noncontagious respiratory mycosis prevalent in the southwest United States. It also is usually self-limited but may lead to chronic pulmonary infection or disseminated infection. Blastomycosis, caused by Blastomyces is a noncontagious, subacute or chronic endemic mycosis most commonly seen in the southeast United States. Most pulmonary infections are probably self-limited. Paracoccidioidomycosis, caused by Paracoccidioides, is a noncontagious respiratory mycosis that is the most common systemic mycosis in South America. It may be acute and self-limited or may produce progressive pulmonary disease or extrapulmonary dissemination. Disseminated disease is generally fatal in the absence of therapy. The present invention addresses the problem of the prior art and provides an effective vaccine and methods of administration.

Cryptococcosis is a noncontagious, often opportunistic mycosis. It is characterized by respiratory involvement or hematogenous dissemination, often with meningitis. A major etiologic agent is *C. neoformans*. Most pulmonary infections are probably overlooked, but cryptococcal meningitis, which accounts for 90% of reported disease, is dramatic and seldom overlooked. Cryptococcosis is a particular problem in immunocompromised patients; cryptococcal meningitis occurs in 7 to 10% of AIDS patients. The principal symptom of meningitis is headache; associated findings include mental changes, ocular symptoms, hearing deficits, nausea, vomiting, and seizures. Without treatment, 80% of patients die within two years. In meningitis, cryptococci can be observed in India ink preparations of cerebrospinal fluid sediment, and can be cultured from the cerebrospinal fluid. Treatment is generally with fluconazole or the combination of amphotericin B and flucytosine, although amphotericin B does not cross the blood brain barrier. The vaccine of the invention is effective against fungal infection in the brain.

Aspergillosis is a term that encompasses a variety of disease processes caused by *Aspergillus* species. *Aspergillus* species are ubiquitous; their spores are constantly being inhaled. Of the more than 300 species known, only a few are ordinarily pathogenic for man: *A. fumigatus, A. flavus, A. niger, A. nidulans, A. terreus, A. sydowi, A. flavatus,* and *A. glaucus*. Aspergillosis is increasing in prevalence and is particularly a problem among patients with chronic respiratory disease or immunocompromised patients. Among immunocompromised patients, aspergillosis is second only to candidiasis as the most common opportunistic mycosis and accounts for about 15% of the systemic mycoses in this group. Opportunistic pulmonary aspergillosis is characterized by widespread bronchial erosion and ulceration, followed by invasion of the pulmonary vessels, with thrombosis, embolization and infarction. Clinically, infection manifests as a necrotizing patchy bronchopneumonia, sometimes with hemorrhagic pulmonary infarction. In about 40% of cases, there is hematogenous spread to other sites. Aspergillosis is also a rare but devastating complication of burn wounds; amputation is often required for cure. Invasive aspergillosis is commonly fatal, so aggressive diagnosis and treatment is required. The vaccine of the invention provides effective therapy against aspergillosis.

Dermatophytosis is a chronic fungal infection of the skin, hair or nails by dermatophytes, which include members of the species *Trichophyton, Microsporum* and *Epidermophyton*. Infection of the foot (tinea pedis), scalp (tinea capitis) are most common, although widespread infection on non-hair-bearing skin (tinea corporis) also occurs. Clinical manifestations vary and may present on the skin as fissuring or lesions with scaling, vesicles or pustules (and alopecia on the scalp), or on the nails as discolored or chalky, crumbling nails. Both topical and systemic therapies may be used to treat dermatophyte infection, including topically administered imidazoles and triazoles (such as itraconazole, miconazole, ketoconzaole and econzaole), haloprogin, undecylic acid, ciclopirox olamine, tolnaftate and terbinafine. Often these chemotherapies fail to provide relief but patients who took the present vaccine are surprisingly responding at higher rate than with conventional therapy.

*Fusarium* species can cause localized or hematogenously disseminated infection (fusariosis), most frequently in patients who have a hemopoietic malignancy and neutropenia. Abrupt onset of fever, sometimes with myalgia, is followed in the majority of cases by distinctive skin lesions resembling ecthyrna gangrenosum. Infection can be treated with amphotericin B but recovery depends ultimately on alleviation of neutropenia. Mortality typically exceeds 90%. The vaccine of the invention does not cause any adverse reactions let alone neutropenia.

Mucormycosis is an acute suppurative opportunistic mycosis that produces rhinocerebral, pulmonary or disseminated disease in immunocompromised patients, and local or disseminated disease in patients with burns or open wounds. Infection is caused by fungi in the class Zygomycetes, and include Basidiobolus, Conidiobolus, Rhizopus, Mucor, Absidia, Mortierella, Cunninghamella, and Saksenaea. Rhinocerebral mucormycosis accounts for about half of all cases of mucormycosis. It is one of the most rapidly fatal fungal diseases, with death occurring within 2-10 days in untreated patients. Early clinical signs include nasal stuffiness, bloody nasal discharge, facial swelling and facial pain. The infection then spreads to the eyes, cranial nerves and brain. Pulmonary mucormycosis is nearly as common as rhinocerebral disease and manifests with the same necrotizing and infarction as aspergillosis. Fungi are virtually never seen or cultured from blood, sputum or cerebrospinal fluid. Disseminated mucormycosis may follow pulmonary or burn wound infection. Treatment is with amphotericin B. In this clinical application the vaccine of the invention is more effective than amphotericin B.

Candidiasis is a general term for a variety of local and systemic processes caused by colonization or infection of the host by species of the yeast *Candida*. Candidiasis occurs worldwide; superficial infections of the skin, mouth and other mucus membranes are universal. Invasive systemic disease has become a problem due to the use of high doses of antibiotics that destroy normal bacterial flora, immunosuppressive agents, and agents toxic to bone marrow, e.g., during cancer therapy. Neutropenia is a major risk factor for *Candida dissemination*. Candidiasis is also seen among immunocompromised individuals such as AIDS patients, organ transplant patients, patients receiving parenteral nutrition, and cancer patients undergoing radiation treatment and chemotherapy. It is the most common opportunistic mycosis in the world. The most common etiologic agent is *Candida albicans*. Other infectious species include *C. tropicalis, C. parapsilosis, C.* stellatoidea, *C. krusei*, *C. parakawsei*, *C. lusitaniae*, *C. pseudotropicalis*, *C. guillermondi* and *C. glabrata*. *Candida albicans* is normally found in the mouth, throat, gastrointestinal tract and vagina of humans. Non-albicans species frequently colonize skin. *Candida* species occur in two forms that are not temperature- or host-dependent. The usual colonizing forms are yeasts that may assume a pseudomycelial configuration, especially during tissue invasion. Pseudomyceliae result from the sequential budding of yeasts into branching chains of elongated organisms. *Candida albicans* contains cell wall mannoproteins that appear to be responsible for attachment of the yeast cells to specific host tissues. *C. albicans* also binds avidly to extracellular matrix (ECM) proteins such as fibronectin, laminin, and types I and IV collagen, all of which contain heparin-binding domains. Clinically, candidiasis manifests as superficial mucocutaneous infections, chronic mucocutaneous candidiasis, or systemic infection. Superficial mucocutaneous infections can occur in any area of skin or mucus membrane. Thrush, commonly seen in AIDS patients, is characterized by a patchy or continuous, creamy pseudomembrane that covers the tongue, mouth, or other oropharyngeal surfaces and may be accompanied by ulceration and necrosis. Intestinal candidiasis is commonly asymptomatic, but is a major source of hematogenous invasion in immunocompromised individuals. Intertrigo involves the axillae, groins, inframammary folds, and other warm, moist areas, and may manifest as red, oozing or dry, scaly lesions. Infections may occur in other areas, including perianal and genital areas. Paronychia, infection of the nails, often follows chronic exposure of the hands or feet to moisture. Some patients with limited T-cell immunodeficiency develop chronic mucocutaneous candidiasis. These patients suffer from persistent superficial *Candida* infection of the skin, scalp, nails and mucus membranes. Most cases of systemic candidiasis are caused by *Candida albicans* and *C. tropicalis*, and increasingly, *C. glabrata*. Clinical manifestations of *Candida* infection appear mainly in the eyes, kidneys and skin. In the eyes, there may be single or multiple raised, white, fluffy chorioretinal lesions. These lesions are a potential cause of blindness. Involvement of the kidneys includes diffuse abscesses, capillary necrosis and obstruction of the ureters. Infection may result in progressive renal insufficiency. Systemic *Candida* infection can also manifest as maculonodular skin lesions surrounded by a reddened area; these lesions have an appearance similar to acne but are a major clue to a potentially lethal disease. Other manifestations of systemic candidiasis may include osteomyelitis, arthritis, meningitis, and abscesses in the brain, heart, liver, spleen and thyroid. Involvement of the lungs is also common, but pulmonary lesions are usually too small to be seen on chest X-ray. Finally, *Candida* endocarditis can occur in patients receiving prolonged intravenous therapy or cardiac valve implants, or in intravenous drug abusers. Fungal lesions appear on the valves, and can embolize and occlude large blood vessels. The mortality rate from systemic candidiasis is about 50%. Systemic candidiasis may be treated with fluconazole, a fungistatic agent, or amphotericin B, a fungicidal agent although systemic use of the latter is limited by its toxicity. Infection of the cornea and conjunctiva, including keratoconjunctivitis, can result from infection by amoeba, viruses, fungi and bacteria. Debilitated patients can develop keratitis from fungi such as *Candida* or *Fusarium* which is often associated with corneal ulceration and can lead to scarring with severe visual loss. Over 80% of patients with *Candida* respond to the therapy with instant composition. common opportunistic mycosis in the world. The most common etiologic agent is *Candida albicans*. Other infectious species include *C. tropicalis*, *C. parapsilosis*, *C. stellatoidea*, *C. kusei*, *C. parakwsei*, *C. lusitaniae*, *C. pseudotropicalis*, *C. guilliermondi* and *C. glabrata*. *Candida albicans* is normally found in the mouth, throat, gastrointestinal tract and vagina of humans. Non-albicans species frequently colonize skin. Candida species occur in two forms that are not temperature- or host-dependent. The usual colonizing forms are yeasts that may assume a pseudomycelial configuration, especially during tissue invasion. Pseudomyceliae result from the sequential budding of yeasts into branching chains of elongated organisms. *Candida albicans* contains cell wall mannoproteins that appear to be responsible for attachment of the yeast cells to specific host tissues. *C. albicans* also binds avidly to extracellular matrix (ECM) proteins such as fibronectin, laminin, and types I and IV collagen, all of which contain heparin-binding domains. Clinically, candidiasis manifests as superficial mucocutaneous infections, chronic mucocutaneous candidiasis, or systemic infection. Superficial mucocutaneous infections can occur in any area of skin or mucus membrane. Thrush, commonly seen in AIDS patients, is characterized by a patchy or continuous, creamy pseudomembrane that covers the tongue, mouth, or other oropharyngeal surfaces and may be accompanied by ulceration and necrosis. Intestinal candidiasis is commonly asymptomatic, but is a major source of hematogenous invasion in immunocompromised individuals. Intertrigo involves the axillae, groins, inframammary folds, and other warm, moist areas, and may manifest as red, oozing or dry, scaly lesions. Infections may occur in other areas, including perianal and genital areas. Paronychia, infection of the nails, often follows chronic exposure of the hands or feet to moisture. Some patients with limited T-cell immunodeficiency develop chronic mucocutaneous candidiasis. These patients suffer from persistent superficial Candida infection of the skin, scalp, nails and mucus membranes. Most cases of systemic candidiasis are caused by *Candida albicans* and *C. tropicalis*, and increasingly, *C. glabrata*. Clinical manifestations of Candida infection appear mainly in the eyes, kidneys and skin. In the eyes, there may be single or multiple raised, white, fluffy chorioretinal lesions. These lesions are a potential cause of blindness. Involvement of the kidneys includes diffuse abscesses, capillary necrosis and obstruction of the ureters. Infection may result in progressive renal insufficiency. Systemic Candida infection can also manifest as maculonodular skin lesions surrounded by a reddened area; these lesions have an appearance similar to acne but are a major clue to a potentially lethal disease. Other manifestations of systemic candidiasis may include osteomyelitis, arthritis, meningitis, and abscesses in the brain, heart, liver, spleen and thyroid. Involvement of the lungs is also common, but pulmonary lesions are usually too small to be seen on chest X-ray. Finally, Candida endocarditis can occur in patients receiving prolonged intravenous therapy or cardiac valve implants, or in intravenous drug abusers. Fungal lesions appear on the valves, and can embolize and occlude large blood vessels. The mortality rate from systemic candidiasis is about 50%. Systemic candidiasis may be treated with fluconazole, a fungistatic agent, or amphotericin B, a fungicidal agent although systemic use of the latter is limited by its toxicity. Infection of the cornea and conjunctiva, including keratoconjunctivitis, can result from infection by amoeba, viruses, fungi and bacteria. Debilitated patients can develop keratitis from fungi such as Candida or Fusarium which is often associated with corneal ulceration and can lead to scarring with severe visual loss. Over 80% of patients with Candida respond to the therapy with instant composition.

Many common ailments are actually dermatophyte infections. Tinea pedis (athlete's foot or ringworm of the feet) is associated with Epidermophyton floccusum, various species of *Trichophyton* and, rarely, species of *Microsporum* and other fungi. Tinea unguium (ringworm of the nails) is caused by *Trichophyton rubrum*. Tinea cruris ("Jock itch" of ringworm of the groin) results from infection with *Epidermophyton floccusum* and species of *Trichophyton*. Tinea corporis (ringworm of the body) is caused by various species of *Trichophyton* and *Microsporum*, involves the smooth and hairless skin and results in either simple scaling or deep granulomas. Tinea imbricata (scaly ringworm) is a disease of the tropics and is apparently caused by a single fungus, *Trichophyton concentricum*. Tinea barbae (barber's itch or ringworm of the beard) is caused by various species of *Trichophyton* and *Microsporum*. Tinea capitis (ringworm of the scalp and hair) is most common in children but may affect adults. The causative organisms, various species of *Trichophyton* and *Microsporum*, may be acquired by contact with infected animals or children. *Microsporum audouini* is most commonly involved but *Microsporum canis* and *Microsporum gypsum* (gypseum) produce deeper, more severe lesions. *Trichophyton tonsurans* is also known to produce widespread infections in the scalp. The significance of skin pH in the development of ringworm is widely known. The susceptibility of humans to ringworm is much greater before puberty than afterwards when the skin pH falls from about 6.5 to about 4.0. This change is largely due to excretion of fatty acids in the sebum and these fatty acids are often highly fungistatic. For this reason, various kinds of topically-applied agents have been used to kill the infecting fungus and relieve the condition. Many treatments for ringworm are based upon alteration of skin pH by topically applying various agents (e.g., propionic acid, undecylenic acid). Other ringworm therapies have relied upon other topically applied commercially available products such as Conofite and Captan. Orally-administered agents (e.g., Griseofulvin and Ketoconazole) are also available.

Unfortunately, however, post-infection treatment cannot completely prevent in many instances. Once therapy is discontinued, reinfection usually occurs. It would therefore be desirable to provide a vaccine against fungus to prevent infection before these adverse effects are suffered. One of the objects of the present invention is to provide a prophylactic vaccine which contains fungal antigen or immunogen and effectively prevents the fungal infection. Preferably this vaccine is oral or delivered transmucosally.

The term "immunogen" or "antigen" as used hereinafter comprises any entity capable of producing a protective antibody or cell-mediated immunological response against a pathogenic organism in an animal. The antigen or immunogen can be whole pathogen or or part of the pathogen including any cell component, a protein, glycoprotein, glycolipid, polysaccharide or lipopolysaccharide which belongs or is associated with the pathogen, or it may be a polypeptide or other entity which mimics all or part of such a pathogen or protein, glycoprotein, glycolipid, polysaccharide or lipopolysaccharide thereof. An example of fungal polysaccharide is schizophyllan.

In general the immunological preparation used according to the present invention comprise by weight 0.0000001 to 20%, and more often 0.000001 to 5% of an immunogen. No specific adjuvant is required as in all other vaccines of the prior art. The precise effective dose is determined by titration or serial dilution of the immunogen to determine the most effective concentration from which the treated patient benefits the most. The dose finding study is a routine clinical exercise well established in the clinical art.

The compounds may also be used to treat infections caused by protozoa such as Toxoplasma, Cryptosporidium, Leishmania, Tripanosoma, Giardia and Trichomonas. For example, they can be used in agriculture or related fields for the control of phytopathogenic fungi such as *Alternaia solani, Blumeria graminis, Botrytis cinerea, Cercospora beticola, Cladosporium herbarum, Corticium rolfsii, Guignardia bidwellii, Helminthosporium tritici repentis, Leptosphaeria nodorum, Magnaporthe grisea* f. sp. oryzae, *Micronectriella nivalis, Monilinia fructigena, Mycosphaerella fijiensis, Mycosphaerella musicola, Mycosphaerella ligulicola, Mycosphaerella pinodes, Phomopsis viticola, Plasmopara viticola, Podosphaera leucotricha, Pseudopeziza tracheiphila, Phytophthora infestans, Puccinia recondita, Pyrenophora teres, Rhizoctonia solani, Venturia inaequalis, Uncinula necator* and *Scierotinia scierotiorum*, in particular for the residual control of *Blumeria graminis, Plasmopara viticola, Puccinia recondita* and *Pyrenophora teres*, and for the curative control of *Puccinia recondita*.

For example the compounds of the invention may be used in combination with one or more other antifungal agents, such as a polyenic derivative e.g. (Amphotericin B, Nystatin, a lipid formulation of Amphotericin B), 5-fluctyosine, an azole derivative e.g. (Fluconazole, Intraconazole, Ketoconazole, Miconazole, Clotrimazole, ZD-08070, UK-109496, SCH 56592), 5-Fluorocytosine, a Pneumocandin or Echinocandin derivative such as Cilofungin, LY-303366, L733560, L-743872 or other cell wall active compound such as Nikkomycin Z, sordarin, steroids, and/or one or more immunomodulating agents such as an interferon e.g. IFN-), interleukine e.g. (IL-1, IL-2, IL-3 and IL-8) and colony stimulating factors, [(G)-CSF, (M)-CSF and (GM)-CSF] and defensins. Particularly advantageous compounds for use with compounds of the invention include Intraconazole, Flucytosine, Fluconazole, Amphotericin B, Natamycin, primaricin, whey, a nd other well known in the art.

The compositions of the present invention can include antiinflammatory steroids. Such steroids are exemplified, but not limited to, Betamethasone dipropionate, Clobetasol propionate, Diflorasone diacetate, Halbetosal, 2 Amicinonide, Desoximetasone, Diflorasone diacetate, Fluocinonide, Halcinonide, Mometasone, Triamcinolone acetonide, 3 Amicinonide, Betamethasone benzoate, Diflorasone diacetate, Fluticasone, Fluocinonide, Halocinonide, Fluocinolone, Flurandrenolide, Halcinonide, Hydrocortisone, Clocortalone, Predincarbate, 6 Aclometasone, Desonide, and/or Methylprednisolone.

Mycoplasmas of veterinary or medical interest include *Mycoplasma bovis, M. gallisepticum, M. agalactiae, M. hyopneumoniae, M. pneumoniae, M. synoviae, M. arthritidis, M. capricolium, M. dispar, M. hominis, M. mycodiessubs capri, M. orale, M. oripneumoniae, M. pulmonis, M. cynos, M. hyorhinis, M. mycoides, M. salvarium* and *M. fermentans*.

A vaccine in accordance with the invention is formulated in conjunction with or without at least one pharmaceutically acceptable carrier. There are numerous and diverse types of acceptable carriers which are readily appreciated by those skilled in the art depending on the route of vaccine administration. While preferred route is oral other routes of vaccine administration that are appropriate in the practice of the invention include rectal, vaginal, intraintestinal, transdermal, intranasal, parenteral, i.e., intramuscular, intraperitoneal, intradermal, intravenous, and implant. Optimized efficacy can be achieved in certain instances by combining two different routes of administration in a course of therapy. For example, intraintestinal administration followed by oral tablets or liquid formulation or intravenous administration followed by intraperitoneal administration.

For oral administration, vaccine can be formulated with a pharmaceutically acceptable solid or liquid carrier. Solid form preparations include powders, tablets, pills, capsules, cachets, and dispersible granules. A solid carrier can be one or more substances which may also act as diluents, flavoring agents, solubilizers, lubricants, suspending agents, binders like calcium and magnesium, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders, capsules and tablets preferably contain from 0.00001 to about seventy percent of the active compound. Suitable carriers are magnesium carbonate, or chloride, magnesium stearate, talc, sugar, lactose, pectin, dextrin, starch gelatin, tragacanth, methylcellulose, sodium carboxymethylcellulose, microcrystalline cellulose, a low melting wax, cocoa butter, and the like.

The term "preparation" as used herein is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills cachets, and lozenges can be used as solid dosage forms suitable for oral administration.

Another type of solid carrier useful in the practice of the invention is a foodstuff. Solid foodstuffs suitable for admixture with a therapeutic dosage or unit dosage of vaccine are, for example, cereals, chewing gum, crackers, candies, meats, vegetable and fruit preparations for babies, and cookies. For veterinary applications, vaccine can be admixed directly into a grain ration or incorporated into a salt block. Likewise, vaccine can be formulated with a liquid foodstuff, for example, milk, infant formula, juices, liquid vitamin supplements, soft drinks, e.g., Coca Cola, and oral rehydration solutions.

Liquid form preparations include solutions, suspensions, emulsions, for example, of water aqueous solution, or other liquids, half-liquid bases, or optionally in pharmaceutically acceptable solvents (e.g., DMSO-propylene glycol solutions).

Also included are solid form preparations which are intended to be converted, shortly before use, to liquid for preparation for oral or rectal administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, thermal converting agents capable of converting solid into liquid at body temperature, and the like.

For intranasal administration of vaccine, the choice of suitable carriers is highly dependent upon the exact nature of the nasal dosage form desired, e.g., solutions, suspensions, ointments, or gels. Nasal dosage forms can generally contain large amounts of water in addition to the active ingredient. Minor amounts of other ingredients such as pH adjusters, emulsifiers or dispersing agents, preservatives (e.g., antimicrobials), surfactants (e.g., non-ionics such as polysorbates) jelling agents, buffering and other stabilizing agents (e.g., antioxidants and metal chelating agents) and solubilizing agents (e.g., solubility enhancers) may also be present. Preferably, the nasal dosage form should be isotonic with nasal secretions. Although vaccine can be formulated in water, more preferably it will be formulated in a solution buffered to a pH of between about 3.0 and 8.0, and most preferably pH 5.0-5.4 using e.g., a buffer system such as an acetate buffer, a phosphate buffer, a citrate buffer, and a succinate buffer.

Formulations suitable for parenteral administration conveniently comprise sterile aqueous preparations of vaccine which are preferably isotonic with the blood of the recipient. Suitable carrier solutions include phosphate buffered saline, saline, water, lactated ringers or dextrose. Such formulations may be conveniently prepared by admixing vaccine with water to produce a solution or suspension which is filled into a sterile container and sealed against bacterial contamination. Preferably, sterile materials are used under aseptic manufacturing conditions to avoid the need for terminal sterilization.

Such formulations may optionally contain one or more additional ingredients among which may be mentioned preservatives (when the formulations are presented in multi-dose containers), buffers to provide a suitable pH value for the formulation, and sodium chloride, or glycerin, to render a formulation isotonic with the blood.

For parenteral administration, vaccine can be used in free or salt form (for example, salts of alkali and alkaline earth metals such as sodium, magnesium and calcium, salts if mineral acids such as HCl and sulfuric acid, or salts of organic acids, such as acetic acid. Amine addition salts can also be used in the practice of the invention, for example a phosphate amine addition salt. Examples of typical carriers are sterilized water, saline, and phosphate buffered saline. Optional additives include isotonic agents, stabilizers, pH controlling agents, agents necessary for the proper infusion of solutions, and water soluble nutrients.

Transdermal administration can be accomplished using preparations in the form of ointments, emulsions, lotions, solutions, creams or transdermal patches. Suitable pharmaceutical carriers for transdermal administration include, for example, polyethylene glycol, propylene glycol, isopropanol, ethanol, oleic acid, N-methylpyrrolidone, sesame oil, olive oil, wood alcohol ointments, vaseline, and paraffin, or mixtures thereof. When vaccine is formulated in a transdermal patch, the therapeutic dose can be incorporated either directly in an adhesive layer that fixes a drug impermeable backing to the skin of the treated-subject, or can be incorporated in a matrix layer and released therefrom in controlled fashion. Suitable adhesive layer carriers for vaccine include, for example, polyisobutenes, polyisobutylenes, polyacrylates, polyurethanes, polysiloxanes, polystyrene copolymers, EVA-copolymer, and polyether amide block copolymers.

Suitable drug-releasing matrices include, for example, natural or synthetic rubbers, polymeric materials, such as EVA copolymers, thickened mineral oil, and petroleum jelly. Optional constituents for the transdermal administration of vaccine include drug permeable rate-controlling membranes and penetration enhancers which are well known to those skilled in the transdermal formulation art.

Suppository administration is particularly well suited for patients with disorders in digestive organs and for infant patients, and affords constant release over an extended period of time. Typical base carriers for suppositories include, for example, natural, synthetic or partially synthetic fats, waxes and derivative thereof from animal, vegetable, or mineral origin. Specific examples include olive oil, corn oil, castor oil, hydrogenated oils, petrolatum, solid paraffin, ligind paraffin, carnuba wax, bees wax, lanolin partially or totally synthetic esters of glycerol fatty acid, mono, di, or triglycerides of saturated or unsaturated fatty acids, and others well known in the art. Other additives suitable for incorporation into a suppository of the invention include preservative, stabilizers, surfactants, pigments, pH modifiers and purified water.

Vaccine can also be made as an implant so that need for frequent administration is not required anymore. A preferred implant matrix is made of a biocompatible, biodegradable, bioabsorbable and/or bioerodible polymeric material that will become gradually disintegrated by the animal's system through enzymatic, chemical and/or cellular hydrolytic action, and release the immunogen for sustained delivery into surrounding tissue fluids over an about 0-2 year period. The implant may be formulated, for example, from cholesterol, cellulosic polymers, polylactide, polycaprolactone, polyglycolide or other like polymers or copolymers thereof. The implant may include immunostimulants such as aluminum hydroxide, muramyldipeptide, lipophilic amines, saponins, Freund's incomplete adjuvant (FIA), polymeric adjuvants, among other adjuvants. The implant may also contain an immunomodulator such as a cytokine, complex carbohydrate, and the like to enhance or modulate the immune response, and other additives as desired, such as preservatives, buffering agents, and the like. Other slow release forms are well known in the art, e.g., dermal patches, pumps, slow release tablets, suppositories, etc., they can be equally suitable to replace the implant.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, lotions, ointments and powders in vials or ampoules. Also, the unit dosage form can be a capsule, tablet, cachet, or lozenge itself, or it can be the appropriate number of any of these in packaged form.

It is also within the scope of the invention to administer vaccine in a time-release formulation such as a bolus for veterinary therapies. A wide variety of methods are now available in the art for preparing time-release or long-acting compositions. Any of these time-release or long-acting formulations are suitable in the practice of the present invention as long as it does not adversely affect the effectiveness of vaccine in the treatment or prevention of fungal infection. Advantages of time-release formulations include a lower concentration of peak serum absorption which substantially reduces any possible adverse side effects and/or toxicity of the active administered. In addition, a reduced frequency of administration results, which substantially improves patient compliance. A frequency of administration of every 12 to 24 hours would be preferred although not necessary. In addition, a more constant concentration of vaccine would result, and consequently, a more consistent relief or prophylaxis of disease symptoms.

Present vaccine will contain pharmaceutically and/or veterinarally acceptable carrier, diluent, excipient and/or adjuvant. These can comprise Marcol 52, Montanide 888, squalane or squalene, Adjuvant 65 (containing peanut oil, mannide monooleate and aluminium monostearate), lipopolysaccharide, mineral gels such as aluminium hydroxide, aluminium phosphate, calcium phosphate and alum, surfactants like hexadecylamine, octadecylamine, lysolecithin, dimethyldioctadecylammonium bromide, N,N-dioctadecyl-N', N'-bis(2-hydroxyethyl)propanediamine, methoxyhexadecylglycerol and pluronic polyols, polyanions like pyran, dextran sulfate, polyacrylic acid and carbopol, peptides and amino acids like muramyl dipeptide, glucan, dimethylglycine, tuftsin and trehalose dimycolate. The antigens, precursors, expression products and/or synthetic polypeptides of the present invention can also be administered following incorporation into liposomes or other micro-carriers, or after conjugation to polysaccharides, proteins or polymers or in combination with Quil-A™. Other adjuvants suitable for use in the present invention include conjugates comprising the immunogen together with an integral membrane protein of prokaryotic origin, like TraT.

When needed the fungal vaccine of the invention can be advantageously combined with other types of vaccines. Such strategy will facilitate spontaneous vaccination programs against several pathogens at once. Contemplated vaccines include but are not limited to: Diphtheria vaccine, Pertussis vaccine, Tetanus vaccine, H. influenzae, *Branhamella catarrhalis, Moraxella catarrhalis, S. pneumoniae*, all serotypes, *E. coli*, endotoxin or J5 antigen (LPS, Lipid A and Gentabiose), *E. coli*, O polysaccharides, *Klebsiella*, polysaccharides, *S. aureus, S. epidermidis*, serotype polysaccharide, I, II and III (and common protective antigens), *N. meningiditis*, serotype specific or protein antigens, Polio vaccine, Mumps, measles, rubella vaccine, Respiratory Syncytial Virus, Rabies, Hepatitis A, B, C, and others, Human immunodeficiency virus I and II (GP120, GP41, GP160, p24, and others like peptide, DNA, chimera), Herpes simplex types 1 and 2, CMV, EBV, Varicella/Zoster, Malaria, Tuberculosis, *Candida albicans*, other candida, *Pneumocystis carinii, Mycoplasma* Influenzae virus A and B, Adenovirus, Group A *streptococcus*, Group B *streptococcus*, serotypes, Ia, Ib, II and III, *Pseudomonas seryinosa* (serotype specific), Rhinovirus, Parainfluenae, types 1, 2 and 3, Coronaviruses, *Salmonella, Shigella*, Rotavirus, Enteroviruses, and *Chlamydia trachomatis*, smallpox, yellow fever, distemper, cholera, fowl pox, scarlet fever, diphtheria, otitis, whooping couch, foot and mouth disease, poliomyelitis and combination thereof.

Instant vaccine can also be combined with anti-parasite vaccines against for example nematodes like *Ancylotoma caninum, Strongylus vulgaris, Trichostrongylus colubriformis, Haemonchus contortus, Ostertagia ostertagi, Ascaris suum, Toxascaris leonina, Uncinaria stenocephala, Trichuris vulpis, Dirofiaria immitis, Toxocara* spp, *Necator americanus, Ancylostoma duodenale, Ascaris lumbricoides, Trichuris trichiura, Enterobius vermicularus, Strongyloides stercoralis* or *Wuchereria bancrofti*.

Without limiting to above parasites instant vaccine can be also used in combination with vaccines against *Plasmodium falciparum*, trypanosomiasis, leishmaniasis, amoebiasis, trichomoniasis, primary amoebic meningitis, chronic acanthamoebic encephalitis and keratitis, babesiosis or combination thereof.

The fungal vaccine preparation of the invention can be combined with a vaccine which contains an antigen from a microbe selected from the group consisting of *Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromatis, Staphylococcus aureus, Vibrio cholerae, Escherichia coli, Pseudomonas aeruginosa, Campylobacter (Vibrio) fetus, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma* spp., *Rick-*

*ettsia prowazeki, Rickettsia tsutsugamushi, Chlamydia* spp., *Helicobacter pylori, Coccidioides immitis, Aspergillus fumigatus, Candida albicans, Blastomyces dermatitidis, Cryptococcus neoformans, Histoplasma capsulatum, Entamoeba histolytica, Trichomonas tenas, Trichomonas hominis, Trichomonas vaginalis, Trypanosoma gambiense, Trypanosoma rhodesiense, Trypanosoma cruzi, Leishmania donovani, Leishmania tropica, Leishmania braziliensis, Pneumocystis pneumonia, Enterobius vermicularis, Trichuris trichiura, Ascaris lumbricoides, Trichinella spiralis, Strongyloides stercoralis, Schistosoma japonicum, Schistosoma mansoni, Schistosoma haematobium,* variola virus, vaccinia virus, cowpox virus, varicella-zoster virus, Herpes Simplex virus 1, Herpes Simplex virus 2, influenza viruses, parainfluenza virus, mumps virus, measles virus, respiratory syncytial virus, rubella virus, Hepatitis A virus, Hepatitis B virus, Hepatitis C virus, Hepatitis E virus, and Non-A/Non-B Hepatitis virus.

The invention also contemplates a method of producing a diagnostic and/or research reagent to detect agents that are characteristic of diseases caused by fungi by immunizing a host with a vaccine described above so that the host produces antibodies or cells-mediated immune response against the agents. The antibodies and/or T cells may be then isolated using standard procedures. Thus, as used herein, diagnostic reagent refers to a composition of antibodies (polyclonal or monoclonal) that may be used to detect agents that are characteristic of diseases. As used herein, research reagent refers to a composition of antibodies (polyclonal or monoclonal) that may be used in the laboratory. Cell-mediated reaction can also be used make diagnostic reagents (e.g., Elispot-type reagent) and to follow the patient's response to immunization

EXAMPLE 1

One method to produce the antifungal preparation is by dissolving or hydrolyzing the suitable fungi by increasing or reducing the pH using methods known in the art. Preferably the pH is above 10 or below 4. Examples of suitable aqueous acids are aqueous solutions of HCl, H2SO4, citric acid and lactic acid. Examples of suitable alkaline solutions are solutions of hydroxides such as NaOH, KOH and NH4OH. The dissolved fungus can be mixed with the suitable carrier or adjuvant compound, like a protein or amino acid. Preferably a food grade proteins is used. Examples of suitable proteins are milk proteins, e.g. whey proteins, caseins and caseinates or other compounds, such as L-glutamine. Also mixtures of different proteins and mixtures of proteins with other compounds such as fats e.g. vegetable and animal fats or oils such as milk fat, butter fat, soya bean oil and sunflower oil can be used. Also compositions or products which contain mixtures of these compounds can be used. Examples of such mixtures are cow milk or soya bean milk. Another example is blood from a normal donor or from fungus-infected patient. After mixing the dissolved fungus with the suitable compound, the pH is adjusted to neutral, e.g., between 5 and 9, preferably between 6 and 8. When the suitable carrier compound was not present, the fungus preparation can crystallize. The presence of the suitable adjuvant can prevent the formation of visible crystals under microscope.

Alternatively the complex of fungus and the suitable compound is made by dissolving the fungus in a suitable solvent system. Suitable solvent systems are lower alcohols such as methanol, ethanol, propanol, ethylene glycol, propylene glycol and glycerol or mixtures thereof. Further, in a suitable alcoholic solvent, one or more hydroxyl groups may be linked by an ester bond to a fatty acid or linked to another alcohol group by an ether bond. Examples of such solvents are methoxy ethanol and ethoxy ethanol. In addition solubilisers such as surfactants can be added to the solvent. Examples of suitable solubilizers are sodium lauryl sulphate, dioctyl sulphosuccinate, calcium chloride or surfactants of the non-ionic type, for instance those which are sold under the trade marks Tween, Span, Brij and Myrj. Adhesion or complex formation between the fungus and the suitable adjuvant or carrier, can be achieved by adding the protein to the solution or vice versa. The protein can already be present in an aqueous environment such as water, milk, or blood. The complex of fungus and the one or more proteins can be used directly in the desired application or can be processed further. For example the complex can be isolated and/or purified using well known methods. Examples of drying methods to separate the complex from a liquid are filtration, centrifugation, evaporation of the liquid, spray drying, freeze drying and fluid bed drying. The purified complex of fungus and one or more proteins is advantageous for the treatment of fungal infections. The complex can be added to edible substances e.g., cheeses or sausages, agricultural products e.g., grain and vegetables. A composition of the invention may also be in the form of an emulsion (e.g. for coating) of the oil-in-water or water-in-oil type. Examples of suitable preparations for treating agricultural products such as fruits are films of polymeric materials such as for example polyolefins, e.g., polyethylene and polypropylene. The amount of fungus in a liquid composition for immersion or spraying treatment may be from 0.00001% to 2% w/v or higher as desired. Preferably the amount is from 0.0001% to 1% w/v. In principle the immersion liquid may be of any kind. When an aqueous system is used, the addition of a surfactant may be of advantage, in particular for treating objects with a hydrophobic surface. Useful surfactants are for example anionic tensides such as sodium lauryl sulphate or polyethylene alkyl ethers such as Cetomacrogol® 1000 or polyoxyethylene ethers e.g. Tween 60, 61 and 65.

EXAMPLE 2

An effective treatment for arresting the growth of undesired microbes in the preparation comprises pasteurization. Pasteurization generally comprises partial sterilization at a temperature and for a period of time that destroys objectionable organisms, without major chemical alteration of the product. To arrest the activity of the bacteria in the composition of the invention, pasteurization can comprise heating the composition to a temperature of at least about 110. degree. F., more preferably at least about 120. degree. F., and maintaining that temperature for at least about 30 minutes. According to the so-called "holding method" or "batch pasteurization", the preparation can be heated to 145. degree. F. and held at this temperature for 30 minutes with constant stirring with an agitator at 60 rpm. Alternatively, a high-temperature, short-time process, can be equally employed. This requires a temperature of 162. degree. F. for as little as approximately 16 seconds. Even shorter duration processes (278. degree. F. for 4-6 seconds, or 285. degree. F. for 2 seconds) can be employed, albeit at added expense. Any combination of time and temperature can be utilized bu those of skill in the art so long as it achieves adequate pasteurization and arrests the undesired microbial growth.

EXAMPLE 3

High-pressure commercially available CO2 gas is an ideal solvent. It has the density of a liquid, but is also highly penetrable and diffusible since it has the properties of a gas at the same time.

EXAMPLE 4

Liquid nitrogen can be used to freeze and to cryogenically grind fungus preparation. For freezing, isolated fungus preparation is immersed into liquid nitrogen for a few (1-15) seconds, with equilibration at 0. degree. F., to form small crystals. This method is often more cost efficient than the use of a mechanical freezer. The resulting cryogenic gas can be recycled in the assembly line as fungus is brought to the freezing equilibrium (e.g. 0. degree. F.). Depending on the needs temperature can vary from −5. degree. F. to −40. degree. F. for less than one minute for grinding in liquid nitrogen. Fungus treated according to the invention can be brought to a temperature as low as −320. degree. F. According to the present invention, fungus is submerged in liquid nitrogen for a sufficient time, generally several minutes. Depending on the strain of fungus, a contact time of 15-30 minutes can be used in order to insure maximal processing. Liquid nitrogen is also viricidal, bactericidal, and fungicidal, particularly at longer and lower cryogenic temperatures.

The freezing the pieces of the desired fungal tissue and lowering its temperature to a critical brittles state will convert the unbreakable, viscous, and sticky material like fungus into an extremely brittle and fragile substance. Brittleness temperature depends primarily on the species and composition of fungal tissue (water, lipids, proteins, carbohydrates, minerals) and therefore its thermal properties. The rate of crystallization (i.e., nucleation and crystal growth) of water will affect the size of crystals. Slow rate of crystallization results in formation of large extracellular water crystals which can cause some rupture of cell membranes, but such effects and even repeated freeze-thaw process have negligible effects in comparison to cell rupture by cryogrinding. It is preferred, however, to keep the physical structure of the tissue cells relatively intact up to the cryogrinding step. This means that, all other factors being equal, the fastest possible freezing rate should be employed.

Once frozen brittle pieces of tissue are obtained, they are transferred to any size reduction equipment such as Waring blender and homogenized (ground) for the desired length of time, i.e., a few minutes at 22,000 RPM. At larger scales, roll mills with both attrition and impact grinding can be used with the same efficiency. It is important that the tissue is kept at or below its brittle temperature throughout the grinding process. Grinding below the brittleness temperature is required in order to produce the necessary small particle size. For this purpose one can add, if needed, sufficient quantities of liquid nitrogen to the sizereduction equipment. Upon completion of the grinding process, an extremely fine, free-flowing and non-sticky cryoground tissue ("fungus powder") is produced. The resultant powder is then can be sieved at or below its brittleness temperature to obtain uniform particles. For this purpose, one of skill in the art can use stacked stainless steel standard sieves. Thus, cryogenic treatment of tissue followed by cryogrinding of the frozen tissue, provides one with materials with very small particle size and enormous surface area in a form suitable for obtaining improved quantities and qualities of desired extracts. While it is clear the above process is highly advantageous the desired material can also be treated with one or any combination of more than one of the following methods of treating the samples including crushing, comminuting, high and low pressure pressing, flaking, sonication, freeze-thaw treatment, emulsification, homogenization, filtration, high speed mixing, centrifugation, mechanical separation and thermal treatments including microwave treatment. Without limiting the sample can be treated with inorganic and organic acids, bases, solvents, surface active agents, colorants, and ionizing radiation. Equally suitable are enzymatic treatments; including endogenous and/or exogenous enzyme reactions.

The cryoground powder then can be further extracted with liquid or super-critical CO2 as a solvent. In one example the solvent to feed ratio of 300 (1 lb./min.) is used. The extractor is maintained at 37. degree. C. at 3500 psig, first separator at 40. degree. C. at about 1500 psig, and second separator at 29. degree.-30. degree. C. at about 1000 psig, where the bulk of extract is collected. The solvent from the second separator is fed into a knock-out vessel at about 1500 psig and then recycled. The residue in the extractor is in the range of 8-17% of the feed. CO2 extracts about 83-92% of the feed which is much higher than for example chloroform/methanol extraction.

While CO2 extraction is easy and simple process one of skill in the art will know that other extraction means can be used to substitute this particular extraction method. Supercritical fluid extraction may be accomplished with many different gases and substances including but not limited Helium; Neon; Argon; Krypton; Xenon; Nitrogen; Hydrogen; Oxygen; Ozone; Fluorine; Ammonia; Boron Trifluoride; Carbon Monoxide; Hydrogen Chloride; Hydrogen Sulfide; Nitric Oxide; Nitrogen Dioxide; Nitrous Oxide; Silane; Silane Chlorotrifluoro; Silicon Tetra Fluoride; Sulfur Dioxide; Sulfur Hexafluoride; Water; Methane; Ethane; Propane; n-Butane; iso-Butane; Ethene (Ethylene); Propene (Propylene); n-Butene; Ethyne (acetylene); Monofluoro Methane; Trifluoro Methane; Tetrafluoro Methane; Monochlorodifluoro; Methane Monochlorotrifluoro; Methane Dichlorodifluoro; Methane Monobromotrifluoro; Methane Monofluoro Ethane; Hexafluoro Ethane; Chloropenatfluoro Ethane; Perfluoro butane; and 1,1-difluro Ethylene among many others.

EXAMPLE 5

In a typical run appropriately diluted fungus culture solution is poured into the batch reactor and the lid is secured. Fungal preparation can be hydrolyzed and reduced as described in Examples above. Carbon dioxide is fed into the reactor until pressures of about 2760 kPa, 4140 kPa or 5520 kPa are reached. The contents of the reactor is then rapidly heated to the desired temperature, thereby increasing the pressure further. The reactor content is then mixed for 30 min. Pressure is released and the reactor content is cooled to 10. degree. C. The resulting slurry is either centrifuged using a Model RC-5B Sorvall Refrigerated Superspeed Centrifuge at approximately 5000 g for 1 hr or filtered over paper or ceramic filter. The precipitate is then washed repeatedly and allowed to dry. Precipitates are usually obtained at temperatures greater than 50. degree. C. and at pressures greater than 2760 kPa. The yield of precipitate increases as the time of reaction increases. pH values during reaction are measured with a highpressure probe designed to withstand pressures up to 6.9 Mpa. pH values decrease dramatically with increasing pressure up to 2760 kPa. The original pH is restored after the depressurization step in the process. The greatest recovery is obtained using conventional salting methods known in the art, but these methods have the disadvantage of contaminating the protein fractions with salt.

EXAMPLE 6

Filamentous fungi are suitable for use in the present invention for the production of antifungal preparation. Preferred filamentous fungi include those of the class known as Oomycetes. Members include *Pythium ultimum* (ATCC 11123), *Pythium debaryanum* (ATCC 9998), *Pythium* sp(ATCC 11270) and *Pythium irregulare* (ATCC 10951) *Pythium irregulare* (ATCC 10951). Preferred fungi are those that cause pathogenesis in humans, e.g., *Aspergillus fumigatus*. Any suitable fermenter can be used in the practice of the present invention. Because filamentous fungi exhibit a strong affinity for adhering to surfaces and for surface colonization, a fermenter designed to take advantage of such properties can be used. The particular type of fermenter used in the practice of the present invention is not critical as long as the fermenter is capable of providing the conditions for filamentous fungi growth. Non-limiting examples of suitable fermenters include submerged culture fermenters, rotating fermentors, as well as the so-called film reactors. Typically, mycelia of a fungus are grown from an inoculum grown in Yeast Maintenance (YM) medium comprised of 3 g/l yeast extract (YE), 3 g/l malt extract (ME), and 5 g/l peptone. The inoculum is macerated for 30 sec at low speed in a Waring-type blender. Two centiliters of the macerated inoculum are added to 100 ml of growth medium in a 250 ml Erlenmeyer flask. The growth medium is 10 g/l spray-dried sweet whey permeate powder (SWP), 3 g/l YE, and 3 g/l $KH_2PO_4$, at a pH of about 6.0. The culture is incubated at 24. degree. C. under orbital shaking at 135 rpm and is harvested at 3-4 days by filtering over filter paper and washed.

EXAMPLE 7

In this example, yeast of the species Candida is cultivated at a temperature of about 25-40. degree. C in a fermentor having a useful volume of approximately 500 liters on a conventional carbohydrate medium to produce about 10 grams per liter per hour of yeast cells. The total hourly output of this fermentor is accordingly 5 kilograms of yeast cells. Fermentor is a closed tank or kettle that is provided with a stirrer driven by an electric motor and includes a mechanical foam breaker in the form of baffle vanes to provide for the separation of gas from the liquid in the foam that may form during fermentation. The fermentor is also provided with cooling elements or heat exchanger through which a coolant is passed. The fermentor is also provided with a pipe for supplying the culture medium or substrate or other nutrients to the fermentor and an outlet pipe is provided for withdrawing the cells of the yeast or other microorganisms that have been grown or cultivated therein. Compressed air is supplied to the fermenting substrate through a pipe from a compressor or blower. The exhaust air or gases are discharged from the fermentor through a pipe that is connected to the mechanical foam breaker. The yeast that is grown in the fermentor is separated from the fermentation brew therein by means of a centrifuge or other suitable apparatus (filter) for separating solids from liquids. The fermentation brew is withdrawn from the fermentor through a pipe that discharges into a separator, from which the concentrated solid fungus in the brew is separated from the liquid portion. Other pathogenic or generally considered non-pathogenic yeast (for example, common yeast *Saccharomyces cerevisiae* causes fungemia in weak and immunosuppressed patients) can be mass-cultivated and used for preparation of the vaccine of the invention.

EXAMPLE 8

In addition to fungus preparation obtained from a fungal culture, one can prepare fungus preparation from any tissue, organs, and cells which host fungal infection. For example, one can select fungus-infected central nervous system tissues and organs (brain, spinal chord, spinal fluid, appendages); peripheral nervous system tissues and organs (cranial nerves, spinal nerves, etc.); myocardial and vascular tissues and organs (heart, arteries, and veins); circulatory tissues and organs (whole blood or components thereof, e.g., erythrocytes, lymphocytes leukocytes, platelets, plasma); lymphatic system tissues and organs (lymph nodes, spleen, thymus); respiratory system tissues and organs (upper respiratory tract, lungs); digestive system tissues and organs (including mouth, teeth, tongue, salivary glands, pharynx, esophagus, peritoneum, stomach, small and large intestine, liver, gall bladder, pancreas); skeletal tissue and organs (axial and appendicular skeleton, bone marrow); muscles (smooth and skeletal); endothelial and epithelial tissue; membranes, cartilage tissues (tendons, ligaments, joints); sensory organs (eyes, ear, nose, tongue); endocrine or other glandular tissue (thyroid gland, parathyroid gland, pituitary gland, adrenal gland); urinary tissue and organs (kidneys, urinary bladder, urethra); reproductive organs and tissues (testes, ovaries, placenta, etc.); and adipose tissues (fat) such as is contained in subcutaneous and internal organs, as well as biological exudates, such as feces, sputum, urine, sweat, mucus, semen, milk, and so forth. In each case processing conditions are chosen which optimizes the physical and rheological characteristics of the desired powder.

EXAMPLE 9

Standard Sabouraud's Dextrose Broth and Sabouraud's Dextrose Agar plates are commercially available suppliers like from Difco and Gibco. SDB is a broth that contains neopeptone and bacto-dextrose in a proportion of 1:4 while SD agar contains neopeptone, bacto-dextrose and agar in proportions of 2:8:3. These fungal culture media may contain adequate small amounts of cyclohexamide and chloramphenicol to prevent concomitant bacterial growth.

A fungal lesion from a human having the desired fungus infection is wiped with 70% alcohol solution and allowed to air dry. The surface of the lesion is then scraped with a scalpel to remove some of the infected skin tissue. The scrapings are then placed in SDB and cultured. After significant growth is observed, a sample from the culture is plated on SD agar plates to check the purity of the sample fungal population. Pure cultures are then used as an inoculate to propagate larger batches of fungi. Alternatively the original inoculate is first subcultured in a separate 10 ml vial containing SDB and then incubated at room temperature for 4 days with constant shaking. Once fungus is grown to maximum the contents of vial is then added to a larger growth chamber containing SDB. The chambers are then grown at room temperature until growth is saturated (i.e., no increase from previous day measured by eye). The chambers are shaken vigorously once a day or shaken constantly in a rotating shaker at 150 rpm. When maximum growth is reached, a sample from each fermentor is plated onto SD plates to check the purity of the cultures. The duration of culture varies with individual fungus species. Maximum growth for *Microsporum canis, Microsporum gypsum* and *Alternaria* sp., is approximately 4 days, 7 days and 4 days, respectively. *T. equinum* when grown in agar plates grows as a flat, buff to brown, granular colony with a reddish-brown reverse pigmentation. Microconidia are produced in great abundance, but macroconidia are rare. *T. mentagrophytes* (var. granulare) grows as a flat, granular, buff colored colony with tannish, brown reverse pigmentation. It produces microconidia in great abundance but macroconidia are infrequent. The organism grows equally well on casein basal agar ("CBA") and CBA supplemented with nicotinic acid. *M. canis* produces abundant macroconidia with prominent surface projections (vesicles) but relatively sparse microconidia. The organism grows as a flat to moderately folded, silky to cottony white surface colony with a yellow reverse pigment. The culture is identified by its pigmentation and typical morphology of its macroconidia. *M. gypseum* grows as a flat granular to velvety buff to orange colored colony that becomes white and cottony with age. The organism produces abundant rough walled (vesiculate) macroconidia and numerous microconidia. The obtained fungal cell mass can be washed, e.g., with sterile distilled water and then disrupted by sonication until 100% of the hyphae are fragmented. Other disruption methods are equally suitable using for example a French press. The fragmented mixture is then centrifuged at 5,000×g for 20 minutes and pellet is processed as described in other examples.

EXAMPLE 10

Alternatively instead of growing fungi of interest in a classical mycotic culture the genes that encode relevant immunogenic proteins or immunogens of fungi of interest can be cloned according to standard molecular biology procedures well known in the art. The genes can be used to express the proteins in an expression vector for example in *E. coli* and combined to provide the starting material for a recombinant vaccine. With advent of recombinant DNA technology it became possible to employ prokaryotic and eukaryotic hosts such as *E. coli*, yeast, fungi, insect, and mammalian cells in culture to produce useful antigens and fragments thereof. For example aspartyl proteinase (Sap2) family of proteins or the 65 kDa mannoprotein (MP65) of *Candida albicans* can be useful antigens to be obtained by recombinant means. The gene encoding for the immunodominant antigen gp43 from the pathogenic fungus Paracoccidioides brasiliensis is another convenient target. *Pneumocystis carinii* p55 antigen or the major surface glycoprotein (MSG or gpA) are yet another attractive antigens. Antigenic Protein 1, referred to as "PMAP1" is an ideal antigen candidate for vaccine against pathogenic fungus *Penicillium marneffei*. The major surface antigen (P30) of the *Toxoplasma gondii* can be expressed in an insect cell culture system infected with recombinant baculovirus. Vector DNA can comprise plasmid, phage or viral DNA and be easily selected from the group consisting of lambda gt11, pUR290, PUR 291, pUR282, pUK270, pUC8, pUC9, pZipNeo, an SV40 based vector, lambda gt10, an EMBL vector, pBR327, pBR329, pBR329 containing a par locus, baculovirus and vaccinia virus among many others. Representative promoters for driving gene expression suitable for use within the present invention include both eukaryotic (e.g., pol I, II or III) and prokaryotic promoters, and inducible or non-inducible (i.e., constitutive) promoters, such as, for example, Murine Leukemia virus promoters (e.g., MoMLV), metallothionein promoters, the glucocorticoid promoter, *Drosophila* actin SC distal promoter, SV 40 promoter, heat shock protein 65 promoter, heat shock protein 70 promoter, immunoglobulin promoters, Mouse polyoma virus promoter ("Py"), nous sarcoma virus ("RSV"), BK virus and JC virus promoters, MMTV promoter, alphavirus junction region, CMV promoter, Adenovirus VAIRNA, rPna promoter, tRNA methionine promoter, CaMV 35S promoter, nopaline synthetase promoter, and the lac promoter among many others. Based on these one can easily imagine a gene expression unit comprising a DNA coding sequence for a fungal heterologous protein and a regulatory element for transcription of said DNA sequence and translation with in a host cell wherein said regulatory element comprises a host-specific promoter. A typical example of mass-producing recombinant fungal antigenic substance is provided as follows. Transformed *E. coli* cells from a culture expressing optimally high levels of recombinant fungal antigens are streaking onto an L-Broth plate containing 100 microg/ml ampicillin and the plate is incubated overnight at 37° C. A single colony is inoculated into 10 ml of L-Broth, 100 microgram/ml ampicillin and grown overnight at 37° C., And aliquot is used to verify plasmid structure by restriction mapping with Sal1 and Pstl. A second aliquot is used to induce expression of fungal antigens and the rest of the culture is made 15% glycerol by adding ¼ volume of 75% sterile glycerol. Glycerol cell stocks are aliquoted in 1 ml and quickly frozen in liquid nitrogen or dry-ice ethanol bath. These master seed stocks are stored at −70° C. When needed the master seed stock is scraped with a sterile applicator which is used to streak an L-Broth plate containing 100 microg/ml amphicillin. Single colonies from this plate are used to inoculate 20-50 ml of L-Broth/amp, which is incubated at 37° C. overnight. An aliquot of the overnight culture is used to inoculate larger volumes (1-6 liters) of L-Broth/amp. Cells are incubated at 37° C. overnight and reach an OD650 of approximately 5 prior to use as inoculum for the fermenter run. Fermenters (capacity about 16 liters) containing 10 l of L-Broth and 1 ml of antifoam are inoculated with 100-500 ml from the inoculum culture. Cells are grown at 37° C. to an or) of about 1. Expression of fungal antigens is induced by addition of 100 ml of an IPTG solution (100 mM) to yield a 1 mM final concentration fermenter. Cells are grown for 3 additional hours and subsequently harvested using continuous flow centrifugation. At this step cells can be frozen and kept at −20° C. until further proceedings. Alternatively, 250 liter fermentors are inoculated with 1-5 liter from the inoculum culture. Growth, induction, and harvest are as indicated before. Frozen *E. coli* cells are thawed and suspended in 2.5 volumes of lysis buffer (0.1M sodium phosphate (NaPi), pH 7.5, 1 mM EDTA, 0.1 M NaCl). Cells are broken in a non-continuous system using a 300 ml glass unit of a Dyno-mill at 3000 rpm and 140 ml of acid-washed glass beads for 15 min. The jacketed chamber is kept cool by a −20° C. ethylene glycol solution. Broken cells are centrifuged at 27,000×g for 25 minutes to remove debris and glass beads. The supernatant is recovered and kept at 4° C. The cell extract is made 30% (NH4)2 SO4 by slowly adding the ammonium sulfate at 4°. The extract is stirred for 10 min after the final concentration is achieved, followed by centrifugation at 27,000×g for 20 min. The pellet is resuspended in 1M NaCl, 1 mM EDTA, 1% Triton X-100™, and 5% SDS, and then boiled for 5 min. The fraction obtained by selective precipitation is submitted to gel filtration using a G50 Sephadex column equilibrated in 0.03M NaPi, pH 6.8. Chromatograpy is developed in the same solution. Fractions are collected and absorbance at 280 inn is determined. Antigen-containing fractions are pooled and characterized by protein gel electrophoresis, Western analysis, and ELISA and are further processed into the composition of the invention. It is also equally possible to use these recombinant antigens without these steps of purification since polyvalent vaccine containing *E. coli* antigens will be equally desirable against enterotoxigenic strains of *E. coli*. Alternatively a process for purifying one or more antigenic or immunogenic substances from a source liquid can comprise steps of contacting the source liquid with a chromatography resin; incubating the soure liquid with the chromatography resin for a sufficient contact time to allow the resin to bind a desired fraction of one or more antigenic substances, recirculating the chromatography resin in a cross-flow filter; concentrating the chromatography resin and separating contaminants from the chromatography-resin-bound antigens by concentration and/or diafiltration; eluting the antigenic substance from the chromatography resin; and separating the immunogenic substance from the chromatography resin by diafiltration; recovering the desired immunogen(s); and optionally concentrating the antigenic or immunogenic fungus-specified substance.

EXAMPLE 11

Yet another recombinant approach is to grow recombinant attenuated fungi and use them for the preparation of the present vaccine. For example pulmonary infection with the dimorphic fungus Blastomyces dermatitidis often progresses and requires treatment to prevent fatality. A recombinant strain of the fungus lacking the WI-1 adhesin gene and accordingly the pathogenicity can be created and propagated in the culture. By mutating a pathogenetic locus in a fungus one can create an attenuated vaccine strain.

EXAMPLE 12

In this example vaccine is prepared against mycoplasma infection. Mycoplasma hyopneumoniae is first propagated in a modification of Friis medium. Each suspension for vaccine incorporation is prepared by inoculating 500 ml of broth with 4 ml of the stock culture at pH 7.4 and then incubated at 37. degree. C. for 3 days or until the pH drops to 6.8. By this time the organism reaches the log phase of growth. The cultures are inactivated using ultraviolet irradiation, concentrated using tangential flow ultrafiltration, and washed with phosphate buffered saline (PBS). The concentration of antigen was adjusted such that it contains 10 mcg of total protein per 1 gram dose of vaccine.

EXAMPLE 13

The vaccine of the invention does not require the express addition of immune adjuvants, which are obligatory with injectable vaccines of the prior art. However, if necessary, one of skill in the art can administer instant vaccine with an immune adjuvant. Typical adjuvants include but are not limited Quil A™ which is a commercially available adjuvant manufactured by Sargent Chemical Co. (Clifton, N.J.) Quil A™ is a purified saponin extract from the bark of the Quillaja Saponaria Molina tree. It is currently used as a suspension medium in a number of large animal vaccines throughout the world, such as the vaccines utilized in the prevention of foot and mouth disease. Quil A™ is widely used, readily available and manufactured by many biologics producers (e.g., Sigma Chemical Co., St. Louis, Mo.). It is comprised primarily of light mineral oil. A number of anhydrous lipid based materials, such as "Lipovant" (Accurate Chemical and Scientific Co., Westbury, N.Y.) which consists of a peanut oil and lecithin mixture is suitable as well. Aluminum hydroxide gel sold by a number of companies including Accurate Chemical and Scientific Co is another suitable immune adjuvant. Other contemplated adjuvants and additives to the formulation include various enterotoxins, tetanus toxoid, saponin, tiabenedezole, tylorone, statolon, maleic anhydride-divinyl ether, a pyran copolymer, amphotericin B, a liposome, silica, calcium phosphate, glycerol betaine, protodyne, cyanidanol, imuthiol, picibanil, isoprinosine lentinan, azimexon, a lecithin, levamisole, a retinol, a tocopherol, an antioxidant, an aluminum salt, and aluminum oxide. The pharmaceutical formulation of instant vaccine can also contain bile salts, surfactants, enzymes, enzyme co-factors, hormones, prostaglandins, peptides, immunoglobulines, cytokines, other vaccines and immunomodulators, antioxidants, amino acids, sources of amino acids and amino acid analogs, antibiotics, vitamins, and minerals.

EXAMPLE 14

The effect of immunization with vaccine of the invention can be tested in vitro. Various methods are available to test immune response to vaccine. One of examples to evaluate cell-mediated response is disclosed as follows: Peripheral blood mononuclear cells (PBMCs) of vaccinated and untreated guinea pigs or of human vaccines and normal non-vaccinated subjects are isolated from the blood samples using Ficoll-Hypaque™ (Pharmacia, Piscataway, N.J.) gradient and centrifuged at 400×g for 30 min. PBMCs that are collected at the interface are harvested and washed twice with RPMI 1640 medium. When needed, the PBMCs are separated into plastic-adherent and non-adherent cells by first incubating 5/10 mln cells in 10 ml of RPMI supplemented with 25 mM HEPES 0.05 mM .beta.-mercaptoethanol, and 10% FCS (v/v). After 2 hours of attachment time, the non-adherent cells are removed and the adherent cells are washed three times with growth medium. PBMCS, non-adherent cells, or adherent cells are seeded at $2 \times 10^5$ cells/100 microL growth medium in 96-well plates and are challenged with isolated fungal antigen of Candida albicans for 6 days in a 37° C., 5% CO2 incubator. For antibody blocking experiments, fungal antigen is pre-incubated with equal volume of human antiserum known to have antibodies to the antigen for 1 hour before being added to the cells, On the $6^{th}$ day, these cells are pulsed with 1 microCi/well of radioactive thymidine for 6 hours to assess the degree of cell proliferation. Radiactive isotope incorporated into cellular DNA is collected on glass fibers with a cell harvester and the degree of proliferation is determined by scintillation counting of radioactivity. Data collected are expressed as mean±SD of the quadruplicates. Those subjects that are vaccinated previously are expected to have greater proliferation response than naïve non-vaccinated individuals. Proliferation test can be easily replaced by cytotoxic lymphocyte (CTL) radioactive Chromium release a test using for example antigen loaded K562 cells as targets for CTL. Another simple technique for detecting the presence or absence of previously exposed T-lymphocytes in a patient's blood consists of incubating the whole blood with the antigen for the suspected fungus being diagnosed, which antigen is dispersed in a suitable pH-regulated medium, such as a buffered saline solution, for example. This incubation will cause previously exposed lymphocytes to become activated. After a suitable incubation period, a fluorescent dye, such as the acetomethylester of the calcium-sensitive dye fura-2, or other colorant having an affinity for activated lymphocytes or lymphoblasts is added to the blood sample. The dye can obtain its attraction to the activated lymphocytes or resultant lymphoblasts through chemical means, by being combinable with the excess calcium ions, or by other means, such as by being tagged with a fluorescently-tagged antibody specific to the transferrin, Leu-23, the surface receptor for T-cell growth factor interleukin-2, or the like. The addition of the dye, colorant, or fluorescently tagged antibody will differentially highlight any responding lymphocytes or lymphoblasts in the blood sample.

Other in vitro and in vivo assays are well know to those of skill in the art including Elispot test, neutralizing antibody measurement test, lactic acid release tests, MTT test, delayed-type hypersensitivity using the footpad swelling response, etc.

EXAMPLE 15

A 11 year-old male patient is presented with a history of progressive headache, mandibular soft tissue swelling, and facial nerve palsy. A computerized tomography scan of the head and neck shows abscesses in the bilateral retromolar fossa and in both ears. A non-sporulating fungus-like organism is isolated in pure culture after surgical drainage of the abscesses. The organism is identified as *Pythium insidiosum*. Despite treatment with amphotericin B, iodides, ketoconazole, and surgery, the infection did not disappear. A magnetic resonance imaging (MRI) and magnetic resonance analysis (MRA) of the neck reveals regional lymph node enlargement, stenosis and aneurysm in the external carotid artery. Surgical removal of the aneurysm is performed and *Pythium insidiosum* hyphae is histopathologically observed in the biopsied tissue. A MRA performed reveals stenosis of the internal carotid artery indicating that *Pythium insidiosum* invaded the artery. The oral vaccine derived from culture *Pythium insidiosum* is administered. Two pills of the vaccine are given per os for 7 days. Remarkably, twenty-four hours post vaccination the patient's headache disappeared, his facial and left tongue swellings dramatically diminished, the enlarged cervical lymph node reduced in size, and the proximal left internal carotid artery stenosis is significantly improved. One year after the vaccination the patient remains free of disease symptoms indicating that fungal infection is cleared due to administration of oral therapeutic vaccine of the invention.

EXAMPLE 16

Approximately 100 patients with HIV infection with oral candidiasis are enrolled to the study. The oral vaccine of the invention is administered to those who have oral thrush. At one and two weeks post-administration of the vaccine the oral cavities of treated patients are examined again for signs of fungal infection. About 80% of patients have cleared or reduced oral thrush.

EXAMPLE 17

5 ml of the final vaccine was administered to cattle on several farms. Depending on the farm, 50-100% of the cattle treated were cured of pre-existing ringworm infection and exhibited resistance to reinfection after treatment. Those infections not succumbing to treatment with the vaccine were probably caused by infecting organisms not included in the vaccine (i.e., other than *Microsporum canis* or *Microsporum gypsum*). 1 ml of the final vaccine also administered to cats. The cats treated exhibited resistance to ringworm infection up to 18 months after administration of the vaccine.

EXAMPLE18

Oral 850 mg pill containing the fungal antigens of the invention formulated by precipitation with magnesium chloride containing 6 molecules of water is administered to twenty police officers who usually wear boots that encourage athlete's foot or pinea pedis growth. Half of officers receive placebo pills and half receive the vaccine. In about one to two weeks those who receive the vaccine have no signs or reduced signs of athlete's foot while in those on placebo the fungal growth is not affected.

EXAMPLE 19

The instant preparation is suitably used along with other antifungals including but not limited to 3,5-dichloro-2,6-dinitrobenzoic acid, 3,5-dibromo-2,6-dinitro benzoic acid, 2,4-dicholoro-3,5-dinitro benzoic acid, methyl 3,5-dibromo-2,6-dinitro benzoate, 1-aminocyclopropane carboxylic acid, L-pyroglutamic acid (5-oxo-2-pyrrolidinecarboxylic acid, albizziin (2-amino-3-ureido-propionic acid), L-phenylalanine ethyl ester, L-tryptophan ethyl ester, L-azetidine-2-carboxylic acid, 2-amino-4-(aminoxy)butanoic acid, 2-aminobutanoic acid, 2-aminohexanedioic acid, 2-amino-4-hydroxybutanoic acid, L-.alpha.-amino-n-butyric acid, 2-amino-4-hydroxybutyric acid, 2-amino-5-hydroxypentanoic acid, 2-amino-4-methyleneglutaric acid, 2-amino-4-methylenepentanedioic acid, 0-[(aminoiminomethyl)amino]homoserine, 2,5-diamino-4-hydroxypentanoic acid, N-(carboxyacetyl)alanine, [(2-amino-2-carboxyethyl) thio]succinic acid, 2,3-diaminopropanoic acid, N.sup.6-(aminoiminomethyl) lysine, 2-amino-5-guanidino-4-hydroxypentanoic acid, N.sup.6-(aminoiminomethyl)-4-hydroxylysine, N-(1H-indol-3-ylacetyl) aspartic acid, beta.-(2,4-dihydroxy-3-pyrimidinyl) alanine, 5-oxo-2-pyrrolidinecarboxylic acid, 2-piperidinecarboxylic acid, N-methylaminoacetic acid, 1,2,3,6-tetrahydro-2-pyridinecarboxylic acid, .alpha.-amino-.beta.-uracil-1-ylpropanoic acid, N-carboxyacetyl-D-phenylalanine, (+)-threo-1-amino-3-methylpentanoic acid, 4-hydroxymethyl-2-pyrrolidinecarboxylic acid, 5-hydroxy-2-piperidinecarboxylic acid, 1-aminocyclopropane-1-carboxylic acid, 2-amino-3-ureido-propionic acid, The following list of fungicides with which instant vaccine can be combined is intended to illustrate possible combinations but not to impose any restrictions. Examples of fungicides which may be combined with compounds of the invention: sulfur, dithiocarbamates and their derivatives, such as ferric dimethyldithiocarbamate, zinc dimethyidithiocarbamate, zinc ethylenebisdithiocarbamate, manganese ethylenebisdithiocarbamate, manganese zinc ethylenediaminebisdithiocarbamate, tetramethylthiuram disulfides, ammonia complex of zinc N,N'-ethylenebisdithiocarbamate, ammonia complex of zinc N,N'-propylenebisdithiocarbamate, zinc N,N'-propylenebisdithiocarbamate and N,N'-polypropylenebis(thiocarbamyl)disulfide; nitro derivative, such as dinitro (1-methylheptyl)-phenyl crotonate, 2-sec-butyl-4,6-dinitrophenyl 3,3-dimethylacrylate, 2-sec-butyl-4,6-dinitrophenyl isopropylcarbonate and diisopropyl 5-nitroisophthalate; heterocyclic substances, such as 2-heptadecylimidazol-2-yl acetate, 2,4-dichloro-6-(o-chloroanilino)-s-triazine, O,O-diethyl phthalimdophosphonothioate, 5-amino-1-[bis(dimethylamino)-phosphinyl]-3-phenyl-1,2,4-triazole, 2,3-dicyano-1,4-dithioanthraquinone, 2-thio-1,3-dithio[4,5-b]quinoxaline, methyl 1-(butylcarbamyl)2-benzimidazolecarbamate, 2-methoxycarbonylaminobenzimidazole, 2-(fur-2-yl)benzimidazole, 2-(thiazol-4-yl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric acid diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine 1-oxide, 8-hydroxyquinoline and its copper salt, 2,3-dihydro-5-carboxanilido-6-methyl-1,4-oxathiyne, 2,3-dihydro-5-carboxanilido-6-methyl-1,4-oxathiyne 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, 2,5-dimethyl-N-cyclohexylfuran-3-carboxamide, N-cyclohexyl-N-methoxy-2,5-diethylfuran-3- carboxamide, 2-methylbenzanilide, 2-iodobenzanilide, N-formyl-N-morpholine-2,2,2-trichloroethylacetal, piperazine-1,4-diylbis-(1-(2,2,2-trichloroethyl)-formamide), 1-(3,4-dichloroanilino)-1-formylamino-2,2,2-trichloroethane, 2,6-dimethyl-N-tridecylmorpholine and its salts, 2,6-dimethyl-N-cyclododecylmorpholine and its salts, N[3-(p-tert.-butylphenyl)-2-methylpropyl]cis-2,6-dimethylmorpholine, N-3-(p-tert.-butylphenyl)-2-methylpropyl]-piperidine, 1-2-(2,4-dichlorophenyl)-4-ethyl-1,3-dioxolan-2-yl-ethyl]-1H-1,2,4-triazole, 1-[2(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N]-imidazolylurea, 1-(4-chlorophenoxy)3,3-dimethyl-1-(1H-1,2,4-triazol-1-yl)-butan-2-one, 1-(4-chlorophenoxy)-3,3-dimethyl-1-(1H-1,2,4-triazol-1-yl)-butan-2-ol, alpha-(2-chlorophenyl)-alpha-(4-chlorophenyl)-5-pyrimidinemethanol, 5-butyl-(2-dimethylamino-4-hydroxy-6-methylpyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)benzene, and various fungicides, such as dodecylguanidine acetate, 3-[3-(3,5-dimethyl-2-oxycyclohexyl)-2-hydroxyethyl]-glutaramide, hexachlorobenzene, DL-methyl-N-(2,6-dimethylphehyl)-N-fur-2-yl alanate, methyl DL-N-(2,6-dimethylphenyl)-N-(2]-methoxyacetyl)-alanate, N-(2,6-dimethylphenyl)-N-chloroacetyl-DL-2-aminobutyrolactone, methyl DL-N-(2,6-dimethylphenyl)-N-(phenylacetyl)-alanate, 5-methyl-5-vinyl-3-(3,5-dichlorophenyl)-2,4-dioxo-1,3-oxazolidine, 3-[3,5-dichlorophenyl]-5-methyl-5-methoxymethyl-1,3-oxazolidine-2,4-dione, 3-(3,5-dichlorophenyl)-1-isopropylcarbamylhydantoin, N-(3,5-dichlorophenyl)-1,2-dimethylcyclopropane-1,2-dicarboximide, 2-cyano-[N-(ethylaminocarbonyl)-2-methoximino]-acetamide, 1-[2-(2,4-dichlorophenyl)pentyl]-1H-1,2,4-triazole, 2,4-difluoro-a-(1H-1,2,4-triazol-1-ylmethyl)-benzhydryl alcohol, N-(3-chloro-2,6-dinitro-4-trifluoromethylphenyl)-5-trifluoromethyl-3-chloro-2-aminopyridine, and 1-((bis-(4-fluorophenyl)-methylsilyl)-methyl)-1H-1,2,4-triazole.

While various embodiments of the present invention have been described hereinabove, it is understood that they have been presented by way of example only and not limitation. Thus, the breadth and scope of the invention should not be limited by any of the above-described exemplary embodiments, but should be defined only in accordance with the following claims and their equivalents.

What is claimed is:

1. A heat-inactivated immunogen formulated as an oral pill comprising a hydrolyzed, dry fungal immunogen, wherein the fungal immunogen is a filamentous fungal antigen and wherein said immunogen upon administration retains the ability to elicit an immune response to said immunogen in a host.

* * * * *